United States Patent [19]

Inoue et al.

[11] Patent Number: 5,955,352
[45] Date of Patent: Sep. 21, 1999

[54] INSTRUMENTS FOR CHEMICAL AND MICROBIOLOGICAL TESTS

[75] Inventors: Yoshiharu Inoue; Yuichi Kinoshita; Mutsumi Shibuya, all of Chuo-Ku; Kiyoshi Oguchi, Shinjuku-Ku; Hiroshi Yamada, Shinjuku-Ku; Chizuko Ohshina, Shinjuku-Ku; Masaho Hayashi, Shinjuku-Ku, all of Japan

[73] Assignee: Showa Yakuhin Kako Co., Ltd., Tokyo, Japan

[21] Appl. No.: 08/879,599

[22] Filed: Jun. 20, 1997

Related U.S. Application Data

[63] Continuation of application No. PCT/JP95/01129, Jun. 7, 1995.

[30] Foreign Application Priority Data

Dec. 22, 1994 [JP] Japan .................................. 6-319805

[51] Int. Cl.$^6$ .................................................. C12M 1/20
[52] U.S. Cl. .................................. 435/287.7; 435/288.4; 435/288.5; 422/58; 422/102
[58] Field of Search .................. 435/287.7, 288.4, 435/288.5, 305.2, 305.3; 422/56, 58, 102

[56] References Cited

U.S. PATENT DOCUMENTS

| | | | |
|---|---|---|---|
| 1,967,557 | 7/1934 | John ............................................. | 88/14 |
| 3,107,204 | 10/1963 | Brown et al. ......................... | 435/288.4 |
| 5,229,163 | 7/1993 | Fox . | |
| 5,244,630 | 9/1993 | Khalil et al. . | |
| 5,338,666 | 8/1994 | Monthony et al. ........................ | 435/34 |
| 5,527,509 | 6/1996 | Gibson et al. ............................. | 422/56 |

(List continued on next page.)

FOREIGN PATENT DOCUMENTS 0 415 679 A2  3/1991  European Pat. Off. .
492 200 A2  7/1992  European Pat. Off. .

(List continued on next page.)

OTHER PUBLICATIONS

Allen, et al., A Noninstrumented Quantitative Test System and its Application for Determining Cholesterol Concentration in Whole Blood, *Clinical Chemistry*, vol. 36, No. 9, 1990, pp. 1591–1597.

Ploum et al., Test strip enzyme immunoassays and the fast screening of nortestosterone and clenbuterol residues in urine samples at the parts per billion level, *Journal of Chromatography*, 564 (1991), pp. 413–427.

Zhujun et al., Poly(vinyl alchohol) as a Substrate for Indicator Immobilization for Fiber–Optic Chemical Sensors, *Analytical Chemistry*, vol. 61, No. 3, 1989, pp. 202–205.

Supplemental European Search Report dated Feb. 14, 1997, issued in a counterpart foreign application of U.S. Appln. No. 08/715,492; filed Sep. 18, 1996 (now allowed).

International Searh Report dated Nov. 9, 1993, issued in a counterpart PCT application PCT/JP93/00157 of U.S. Appln. No. 08/387,893; filed Feb. 21, 1995 (now allowed as 08/715,492).

*Primary Examiner*—William H. Beisner
*Attorney, Agent, or Firm*—Pillsbury Madison & Sutro LLP

[57] ABSTRACT

An instrument for chemical and microbiological tests comprises a sample container for temporarily storing a liquid sample; a plurality of sample-holding portions formed on the bottom face of the sample container; and a liquid-absorbent body capable of coming in contact with the liquid sample so that the body can absorb the excess sample, when the liquid sample is introduced into the container, while retaining the sample to be held on the sample-holding portions. This instrument can be used in a chemical or microbiological test wherein a sample is used in a relatively small amount and, in particular, those requiring a large number of reactions and cultivation. Moreover, the instrument does not require the dispensation of a sample to each reaction system and does not cause any scatter of the sample in the surroundings.

10 Claims, 10 Drawing Sheets

U.S. PATENT DOCUMENTS

| | | | |
|---|---|---|---|
| 3,497,320 | 2/1970 | Blackburn et al. | 23/230 |
| 3,992,158 | 11/1976 | Przybylowicz et al. | 23/253 |
| 4,038,030 | 7/1977 | Albright et al. | 23/230 |
| 4,087,332 | 5/1978 | Hansen | 195/127 |
| 4,153,512 | 5/1979 | Messner et al. | 195/103.5 K |
| 4,260,392 | 4/1981 | Lee | 23/230 |
| 4,483,925 | 11/1984 | Noack | 422/104 |
| 4,738,823 | 4/1988 | Engelmann | 422/56 |
| 4,818,677 | 4/1989 | Hay-Kaufman et al. | 435/4 |
| 4,898,529 | 2/1990 | Muchnik et al. | 425/542 |
| 4,904,605 | 2/1990 | O'Brien et al. | 436/169 |
| 4,994,238 | 2/1991 | Daffern et al. | 422/56 |
| 5,041,266 | 8/1991 | Fox | 422/102 |
| 5,047,322 | 9/1991 | Emmons et al. | 435/6 |

FOREIGN PATENT DOCUMENTS

| | | |
|---|---|---|
| 0 656 420 | 6/1995 | European Pat. Off. . |
| 50-145576 | 11/1975 | Japan . |
| 50-38717 | 12/1975 | Japan . |
| 52-154589 | 12/1977 | Japan . |
| 53-21677 | 7/1978 | Japan . |
| 55-44599 | 11/1980 | Japan . |
| 60-222770 | 11/1985 | Japan . |
| 61-96999 | 5/1986 | Japan . |
| 62-103542 | 5/1987 | Japan . |
| 62-182652 | 8/1987 | Japan . |
| 63-219397 | 9/1988 | Japan . |
| 2-6541 | 1/1990 | Japan . |
| 3-49695 | 3/1991 | Japan . |
| 3-61857 | 3/1991 | Japan . |
| 3-282257 | 12/1991 | Japan . |
| 4-18351 | 1/1992 | Japan . |
| 4-228062 | 8/1992 | Japan . |
| 4-265860 | 9/1992 | Japan . |
| 4-315946 | 11/1992 | Japan . |
| 58-209995 | 12/1993 | Japan . |
| 6-181745 | 7/1994 | Japan . |

INSTRUMENTS FOR CHEMICAL AND MICROBIOLOGICAL TESTS

This is a Continuation of: International Appln. No. PCT/JP95/01129 filed Jun. 7, 1995 which designated the U.S.

TECHNICAL FIELD

The present invention relates to an instrument suitably used in chemical tests or microbiological tests.

BACKGROUND ART

There have usually been used a plastic microplate provided thereon with a plurality of wells as a reaction vessel or a culture vessel in a chemical test which comprises a process for reacting a chemical sample with a certain reagent, or a microbiological test which comprises a step for cultivating a microorganism in a sample, in particular, in a test which requires treatments of a number of samples, reactions with a number of reagents or cultivation of a microorganism in a number of systems.

For instance, a plastic plate equipped with a number of small wells has usually been used in immunological assays such as ELISA assays. In respect of the determination of the sensitivity of bacteria to antibacterial agents by the micro liquid dilution technique, i.e., the determination of the minimum inhibitory concentration (MIC) for a specific antibacterial agent, there has widely been used the single disc method according to the agar plate dilution method or the agar diffusion method, but the use of a microplate provided with U-shaped wells identical to that used in the immunological tests is specified, in the standard method for the determination of MIC by the micro liquid dilution technique which is designated by the Chemotherapeutic Association of Japan in 1989, which is similar to the foregoing single disc method further economized and automated.

In such a test wherein a microplate is used, individual reactions or cultivation of microorganisms each is carried out in a separate well on the plate. In the determination of MIC by the micro liquid dilution method using a microplate, for instance, an antibacterial agent is added to a plurality of wells in a variety of concentrations and the growth of a bacterium to be tested in each well is then observed to thus determine the minimum inhibitory concentration of the antibacterial agent. As microplates used in such tests, there have been put on the market one which is prepared by preliminarily dispensing a desired amount of an antibacterial agent to each well and then drying or freezing and storing. However, the microplate per se is expensive, this makes it difficult to offer a cheaper commodity and accordingly, the users have strongly desired for the reduction of the price thereof. Moreover, such a microplate requires the dispensation of a desired amount of, for instance, a liquid sample to each well during testing and it requires a tremendous labor to carry out the test. Accordingly, it is preferred to develop an instrument for easily dispensing, for instance, a desired amount of a liquid sample to a container used for carrying out the desired test.

To meet such a demand, the inventors of this invention have proposed an instrument for use in chemical tests or microbiological tests, which comprises a base provided thereon with portions for holding a sample (WO 94/04703). The instrument is designed to absorb, for instance, a liquid sample in the sample-holding portion formed on the base to hold a desired amount of the liquid sample on or within the sample-holding portion and to thus meet the foregoing requirement. To allow the instrument to hold a sample, however, it should be designed in such a manner that an excess of the sample is dropwise added to the instrument and then it is, for instance, inclined to remove the excess sample; or the instrument per se is immersed in a liquid sample accommodated in a container and then pulled up to thus allow the sample-holding portion to hold a desired amount of the sample.

For this reason, the liquid sample is inevitably scattered in the surrounding to some extent when using the foregoing instrument to carry out such a test. However, any scattering of the liquid sample should sometimes be avoided when the liquid sample to be tested comprises, for instance, pathogens.

DISCLOSURE OF THE INVENTION

Accordingly, an object of the present invention is to provide a test instrument which is not expensive and can be used in chemical tests or microbiological tests wherein a sample is used in a relatively small amount and, in particular, which require a large number of reactions, cultivation or the like and more specifically, to provide a test instrument in which a sample must not be dispensed to each reaction system and which can prevent any scattering of the sample in the surroundings.

The inventors of this invention have further improved the test instrument disclosed in the patent application filed by the inventors (WO 94/04703) to thus provide a test instrument which is designed such that an excess of a liquid sample is once fed onto the sample-holding portion, followed by absorption of the excess liquid sample with a liquid-absorbent body to thus leave a desired amount of the liquid sample on the sample-holding portion and accordingly, the foregoing problems have been solved.

According to the present invention, there is thus provided an instrument for chemical and microbiological tests which comprises a sample container for temporarily storing a liquid sample; a plurality of sample-holding portions formed on the bottom face of the sample container; and a liquid-absorbent body capable of coming in contact with the liquid sample so that the body can absorb the excess sample, when the liquid sample is introduced into the foregoing container, while retaining the sample to be held on the sample-holding portions.

BEST MODE FOR CARRYING OUT THE INVENTION

Figure 1:
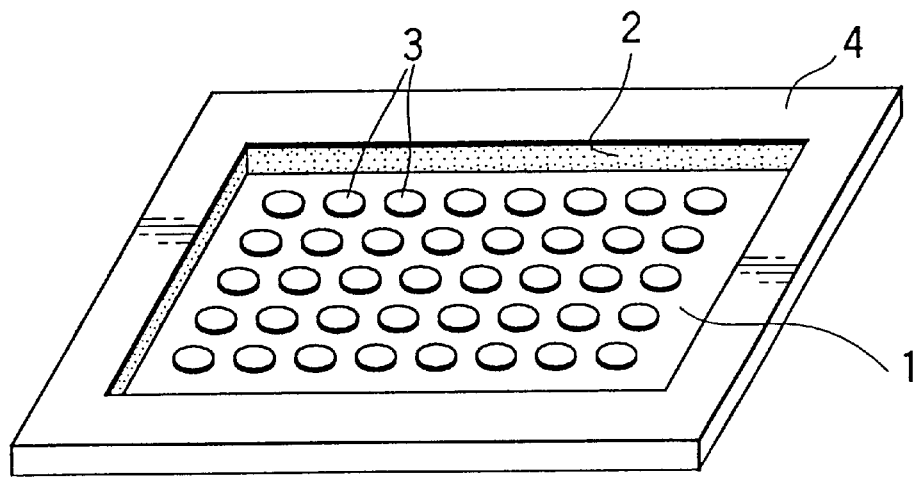
FIG. 1 is a perspective view schematically illustrating the instrument for tests according to a first embodiment of the present invention.

In an embodiment of the present invention, the sample-holding portions are provided on the bottom face of the foregoing container in the form of hydrophilic portions.

In another embodiment of the present invention, the sample-holding portions are provided on the bottom face of the foregoing container in the form of recess wells.

In an embodiment of the present invention, the liquid-absorbent body is formed in such a manner that it constitutes a part or the whole of the inner wall of the sample container for accommodating a liquid sample. In this embodiment, the test instrument of the present invention comprises a base having sample-holding portions and a liquid-absorbent body arranged on the base, wherein the inner botton face of the sample container for accommodating the liquid sample may be defined by the face of the base on which the sample-holding portions are formed and the inner side face of the foregoing container may be defined by the foregoing liquid-absorbent body.

In another embodiment of the present invention, the liquid-absorbent body is provided so as to constitute a part of the whole of the inner bottom face, except for the sample-holding portions, of the sample container for accommodating a liquid sample.

In a further embodiment of the present invention, the test instrument can be designed such that the periphery of the sample-holding portion is positioned at a level higher than that of the portion on the bottom face of the container other than the sample-holding portions. In this embodiment, the liquid-absorbent body may be formed in such a manner that it constitutes the lowest portion of the bottom face of the container except for the sample-holding portions.

In a still further embodiment of the present invention, the test instrument further comprises a cap body of the sample container for accommodating the liquid sample and the liquid absorbent body can be positioned on the internal surface of the cap body so that, when the cap body is fitted to the container, the liquid-absorbent body can absorb the excess of the sample other than the sample to be retained on or within the sample-holding portions.

In a still another embodiment of the present invention, the test instrument further comprises a bottom member arranged behind the sample container and capable of supporting the liquid-absorbent body, the bottom member defines a region for accommodating the liquid-absorbent body in cooperation with the sample container, the sample container is provided with a peripheral portion positioned below the sample-holding portion and a through hole formed on the peripheral portion, and the through hole permits the fluid communication with the liquid-absorbent body-accommodating region arranged between the sample container and the bottom member.

In an embodiment of the present invention, the outer peripheral edge of the sample-holding portion is positioned at a level higher than that of the peripheral portion thereof and the peripheral portion may be formed from a funnel-like wall body which downward extends from the outer edge towards the hole.

In an embodiment of the present invention, the bottom member may be provided with a plurality of upward extending cylindrical standing-up walls and the top face of the standing-up wall may have a shape substantially complementary to the lower face of the sample-holding portion.

In one embodiment of the present invention, the bottom member is realized in the form of a container whose top is opened, a plurality of cylindrical standing-up walls which upward extend are formed on the bottom wall of the bottom member, the top face of the standing-up wall constitutes the sample-holding portion, there are formed a plurality of through-holes on the liquid-absorbent body, through which the standing-up wall may pass and there may be formed, on the bottom face of the container, a plurality of openings capable of being fitted to the top portions of the standing-up walls.

In an embodiment of the present invention, an upper projection which supports the liquid-absorbent body is arranged on the bottom wall of the bottom member and the projection may be positioned below the through-hole.

In one embodiment of the present invention, the standing-up wall is realized in the form of a cylinder and a stepped portion is formed on the outer periphery of the standing-up wall, which is fitted with the inner peripheral edge of the opening on the bottom face to thus arrange the top edge of the standing-up wall and the bottom face on a substantially the same plane.

In one embodiment of the present invention, the sample-holding portions may comprise an agent for use in a chemical test or for a microbiological test.

The test instrument of the present invention has a sample container for temporarily storing a liquid sample and thus the liquid sample may be injected into the container and may be stored therein. In addition, a plurality of sample-holding portions are provided on the inner bottom face of the container. Further the test instrument of the present invention comprises a liquid-absorbent body which is designed in such a manner that, when a liquid sample is injected into the sample container, the liquid-absorbent body may constitute at least a part of the inner surface of the portion of the container in which the liquid sample is accommodated or that the liquid-absorbent body can come in contact with the liquid sample through other methods. The liquid-absorbent body gradually absorbs the liquid sample accommodated in the container. If the excess liquid sample is gradually removed in this way, only a desired amount of the liquid sample can be retained in the sample-holding portion by the method as will be detailed below, any liquid sample does not remain on the inner bottom surface of the container other than the sample-holding portions and this accordingly permits the formation of, for instance, a reaction system wherein the liquid sample is retained in the sample-holding portions in a predetermined amount.

Accordingly, the use of the test instrument of the present invention can eliminate the need for dispensation of a sample to each reaction system and the need for spraying of the sample on the instrument or for dipping the instrument in the liquid sample. This can in turn prevent any scattering of the sample in the surroundings.

The present invention will hereinafter be explained in more detail with reference to the following specific embodiments.

Figure 2:
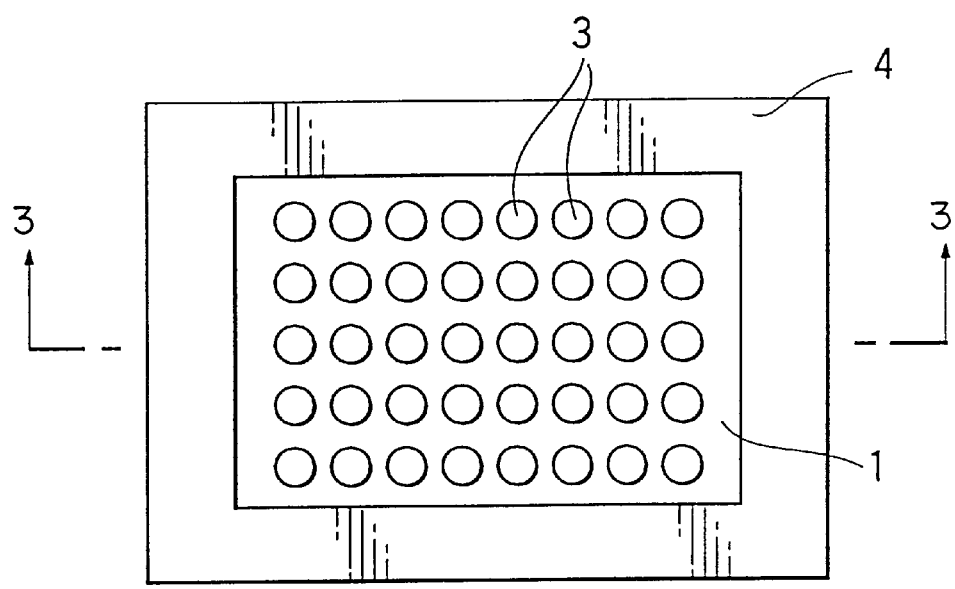
FIG. 2 is a top plan view showing the test instrument as shown in FIG. 1.
Figure 3:
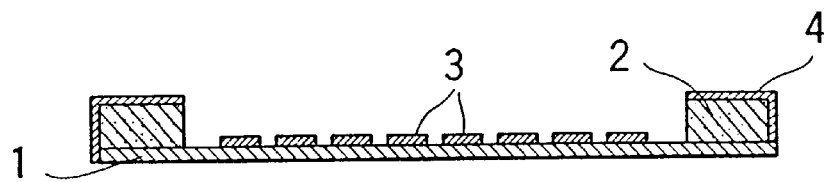
FIG. 3 is a cross sectional view of the test instrument as shown in FIG. 2, taken along the line AA' in FIG. 2.

FIG. 1 is a perspective view of the instrument for tests according to a first embodiment of the present invention, FIG. 2 is a top plan view of the test instrument as shown in FIG. 1 and FIG. 3 is a cross sectional view of the test instrument as shown in FIG. 2, taken along the line AA'. The test instrument of the present invention shown in FIGS. 1 to 3 comprises a base 1 which constitutes the bottom face of a sample container and a liquid-absorbent body 2 which is mounted on the base and constitutes the side face of the sample container. In short, the sample container is constituted by the base 1 and the liquid-absorbent body 2 in this embodiment. In addition, a plurality of sample-holding portions 3 are provided on the bottom face of the sample container formed by the base 1.

In the test instrument shown in FIG. 1, the sample-holding portions each is realized in the form of a hydrophilic portion on the bottom face of the sample container and the portions on the bottom face of the container except for the sample-holding portions are hydrophobic (or water repellent) in nature.

A liquid sample is injected into the sample container defined by the foregoing base and the liquid-absorbent body to thus fill the container with the sample. Then the liquid-absorbent body starts to absorb the liquid sample, only the liquid sample is finally retained on the hydrophilic sample-holding portions or the liquid sample is retained only on each hydrophilic sample-holding portion in the form of a liquid drop which rises due to its surface tension, while the liquid sample is not retained at all on the surface of the container except for the sample-holding portions, i.e., water repellent portions to thus form a reaction system on or within the sample-holding portions.

The base of the test instrument of the present invention may be produced from any material, but materials therefor may be selected from the group consisting of, for instance, polymers such as polyethylene, polypropylene, ethylene-vinyl acetate copolymer, ethylene-vinyl alcohol copolymer, polystyrene, polyacrylate, polyvinyl chloride, polyvinyl alcohol, polyvinyl butyral, polyamide, polyester, polycarbonate, polyurethane, polyimide and triacetyl cellulose; metal sheets such as aluminum and stainless steel sheets; films; and paper laminated with the foregoing polymers, while taking into consideration, for instance, strength, processing characteristics and prices thereof.

The size, thickness and shape of the base are not restricted to specific ones and may arbitrarily be selected depending on the procedures of a particular test used such as the size, number and shape of the sample-holding portions to be formed thereon, as well as the size of the liquid-absorbent body fitted to the base, or in such a manner that each material selected can provide appropriate handling properties. Preferably, the base is in general formed into a rectangular plate-like shape, for instance, a rectangular shape generally having a side ranging from 2 to 10 cm, a length of 5 to 15 cm and a thickness ranging from 0.1 to 2 mm. The materials for the sample-holding portions and the base may likewise have an appropriately selected color, a degree of transparency or the like so as to render any change indicative of test results such as the growth of bacteria and the progress of a color reaction easily detectable. For instance, transparent and black-colored bases may be used in the invention.

It is preferred to select a relatively high hydrophobic substance as the material for the base. This is because a desired degree of the contrast in water repellency between the sample-holding portions and the other portions can easily be ensured simply by providing hydrophilic sample-holding portions thereon without subjecting the base to a water-repellent treatment. If the base has relatively high hydrophilicity, it is sufficient to subject the portions other than the sample-holding portions to a water-repellent treatment.

The hydrophilic sample-holding portions may be formed by pasting or coating the base with a substance having hydrophilicity or water absorption properties.

In the test instrument of the present invention, the reaction system or cultivation system or the like may mainly be held in the sample-holding portions through absorption or may be retained on the sample-holding portions in the form of liquid drops.

Incidentally, the term "sample-holding portion(s)" referred to in the present invention is not restricted to mean only the portions for holding samples to be inspected, but embraces those for holding any reaction system or cultivation system used in desired chemical or microbiological tests.

Moreover, the sample-holding portion may simply be a hydrophilic or water-absorbing portion, i.e., a portion free of any reagent, but preferably the sample-holding portions comprise, from the beginning, reagents required for these tests in order to make the most use of such an advantage of the test instrument according to the present invention that a desired amount of a liquid sample may easily be dispensed by the method described above. For instance, if the instrument is used as a means for determining the sensitivity of bacteria to an antibacterial agent according to the aforementioned micro liquid-dilution method, the determination of the sensitivity of bacteria to an antibacterial agent can be carried out simply by adding a bacteria-containing liquid obtained by suspending a desired amount of bacteria in an appropriate culture medium to sample-holding portions during the test if a desired amount of an antibacterial agent to be tested is previously included in the sample-holding portions. In this respect, however, the reagents are maintained on or within the sample-holding portions in such a manner that the reagents are not released immediately after the injection of a liquid sample into the sample container, but released after the excess sample is substantially removed while leaving a desired amount of the sample on or within each sample-holding portion.

Moreover, if the instrument is, for instance, used as a tool for the determination of the sensitivity to an antibacterial agent and the instrument is provided with a plurality of sample-holding portions which can retain the same amount of a culture medium and the content of an antibacterial agent is stepwise changed, the determination may easily be performed by dispensing a predetermined amount of a bacterial sample to each sample-holding portion of the test instrument as has been explained above and then observing the growth conditions of the bacteria. It is preferred for the purpose of the foregoing test to adjust the content of the antibacterial agent such that it is doubled from one sample-holding portion to another portion.

The sample-holding portions may be formed by the same method used for forming the sample-holding portion of the test instrument disclosed in the foregoing patent Application of the inventors of this invention (WO 94/04703). In this connection, all of the disclosure of WO 94/04703 is, by reference, incorporated into the present specification as a part of the description thereof.

Examples of materials usable in the present invention for forming the sample-holding portions are fibrous substances having water absorbing properties and water retention characteristics such as filter paper and pulp disk; sponge-like porous substances produced from various kinds of polymers; polysaccharides such as starch, agar and pullulan; proteins such as casein and gelatin; cellulose derivatives such as crystalline cellulose, methyl cellulose, ethyl cellulose, carboxymethyl cellulose, hydroxyethyl cellulose and hydroxypropyl cellulose; various kinds of polymers such as polyvinyl alcohol, polyethylene glycol, polypropylene glycol, polyacrylamide, polyacrylic acid, poly(sodium acrylate) and polyvinyl pyrrolidone and copolymers thereof which may, if necessary, be copolymerized with other monomers; products commercially available from Dai-ichi Kogyo Seiyaku Co., Ltd. under the trade name of PAOGEN which mainly comprise polyethylene glycol and polypropylene glycol or partially cross-linked products thereof; naturally occurring adhesives such as gum arabic; and mixture thereof.

Among the foregoing materials, polyvinyl pyrrolidone, hydroxyethyl cellulose, hydroxypropyl cellulose, polyethylene glycol, polyvinyl alcohol, PAOGEN or the like show a high effect of thickening a sample when absorbing the sample liquid and as a result, the viscosity of the sample held on the sample-holding portion is increased upon practical use. The sample is thus firmly maintained and hardly released from the sample-holding portion during handling the same and therefore, the use of such materials is preferred in the invention.

The use of water-absorbing gel as the material for forming the sample-holding portions is more preferred for the foregoing purpose of the firm retention of the sample.

Examples of water-absorbing gels preferably used herein are polyvinyl alcohol/polyacrylate type gels, cross-linked polyacrylate type gels, cross-linked polyvinyl alcohol type gels, cross-linked polyethylene oxide type gels, cross-linked polyacrylamide type gels such as cross-linked polydiethyl acrylamide gels and cross-linked polyisopropyl acrylamide gels, cross-linked polyvinyl pyrrolidone type gels and cross-linked PAOGEN gels. These water-absorbing gels may be used alone or in any combination thereof.

When using such a water-absorbing gel as the material for forming the sample-holding portions, they are in general used in combination with an appropriate binder.

Examples of materials usable as such binders include hydrophobic resins (water-insoluble resins), for instance, acrylic resins such as those commercially available from Mitsubishi Rayon Co., Ltd. under the trade mark "Dianal" BR-Resin, polyvinyl butyral, polyester resins, polyurethane resins, fluoroplastics, silicone resins and styrene-butadiene latex resins, and resins soluble in water and simultaneously soluble in organic solvents (soluble in both aqueous and organic solvents) such as polyvinyl pyrrolidone and hydroxypropyl cellulose. These binders may likewise be use alone or in any combination thereof.

The size, shape, position on the base or the like of the sample-holding portions are not restricted to specific ones and can arbitrarily be selected depending on, for instance, the materials for the sample-holding portions, which are also selected such that the portion can hold a desired amount of the reaction system or cultivation system required for each particular test as well as the method for preparing the test instrument of the present invention.

The use of, for instance, fibrous materials such as filter paper and sponge-like porous materials permits the formation of the sample-holding portions capable of holding a relatively large amount of a sample. In this case, the sample-holding portion in general has a circular shape having a diameter ranging from about 3 to 20 mm or a rectangular shape whose side has a length ranging from 3 to 20 mm and the thickness of the sample-holding portion ranges from about 0.5 to 3 mm. In this case, the amount of the sample to be accommodated in each sample-holding portion in general ranges from about 0.005 to 0.1 ml.

If materials such as polymers and water-absorbing gels are used, the sample-holding portions can easily and effectively be formed by, for instance, printing techniques and further fine sample-holding portions may likewise be formed easily. For instance, there can be formed fine sample-holding portions each having an area of about 5 $mm^2$ and a distance between neighboring two such portions of about 0.5 mm. Moreover, sample-holding portions having a thickness, as determined after drying, ranging from about 0.01 to 500 $\mu$m by a single printing operation. The amount of a sample capable of being retained in such a sample-holding portion in general ranges from about 0.005 to 0.1 ml.

In addition, if polymers and water-absorbing gels such as those listed above are used as the materials for the sample-holding portions, the polymer and/or the water-absorbing gel and, if necesary, an appropriate binder can be dissolved or dispersed in an appropriate solvent, followed by applying the resulting solution or dispersion onto the base in a desired pattern or dropping it on the base using a dispenser and then drying to thus give the instrument of the present invention.

More preferably, the test instrument of the present invention can be produced by forming the sample-holding portions on the base according to a printing technique such as the screen process printing and the gravure printing technique using, for instance, a solution of the materials listed above for the sample-holding portions in an appropriate solvent as an ink, followed by drying. The printing techniques used in the production of the test instrument may be any printing technique used for the preparation of the usual printed matter, with the screen process printing and the gravure printing techniques being particularly preferred.

If the sample-holding portions are formed by printing as discussed above, it is preferred to form the sample-holding portions prior to the arrangement of the liquid-absorbing body on the base. Alternatively, sample-holding portions may be formed on a sheet-like material, followed by pasting the sheet-like material on the inner bottom face of a sample container. Such a sheet-like material may be selected from those listed above in connection with the base.

When the sample-holding portions are formed by printing, the arrangement, shape, thickness or the like of the sample-holding portions may be controlled by the shape of the printing block used and it is also possible to form sample-holding portions having different thicknesses through a single printing operation. In this connection, if the sample-holding portions having a desired thickness cannot be formed by a single printing operation, the sample-holding portions having a desired thickness may be prepared by repeating the same printing operation over a plurality of times.

Another method for producing the instrument of the present invention according to the printing technique may comprise, for instance, forming, in advance, parts which serve as partition walls (each separating two neighboring sample-holding portions) on the base according to the printing technique, followed by charging a material for forming the sample-holding portions to the portions on the base defined by the partition walls to thus give a test instrument according to the present invention. In this case, the foregoing partition wall must be hydrophobic (or water-repellent).

For instance, the test instrument of the present invention can be produced by forming, according to the foregoing printing technique, a lattice pattern or the like which defines independent portions for subsequently forming the sample-holding portions on a base composed of an appropriate material; injecting a material for forming the sample-holding portions, for instance, a solution of, for instance, the foregoing polymer material in an appropriate solvent into each independent portion formed by the pattern; and then drying.

The formation of the sample-holding portions by the printing techniques as has been discussed above is preferred not only for the reduction of the price of the test instrument per se through mass-production but also suitable for the formation of fine sample-holding portions as well as the formation of sample-holding portions which correctly comprise a desired amount of a reagent required for carrying out the test and, in particular, it is suitable for the production of a test instrument provided with a large number of sample-holding portions and accordingly adapted for the automation of the test.

As has been discussed above, the reagents required for the test may be added, in advance, to the sample-holding portions by impregnating the sample-holding portions with a solution containing such a reagent and then drying when using, for instance, a fibrous material such as filter paper or a sponge-like porous body; or by adding such a reagent to a solution or dispersion of a polymer or the like, which is subsequently applied to the base, when using such a polymer.

In the latter case, the reagent is admixed with a solution or dispersion of, for instance, the foregoing polymer or water-absorbing gel to thus give a mixed liquid serving as an ink, applying the ink onto the base by a variety of printing processes and then drying to easily and effectively form a large number of sample-holding portions.

If the sample-holding portions are formed by printing, a multi-layered sample-holding portions comprising a plurality of reagents can be formed by carrying out the printing operation over a plurality of times using inks comprising different reagents and a material for forming the portions. It is also possible to form sample-holding portions comprising different contents of a reagent by carrying out printing operation over a plurality of times using the same ink comprising a reagent and a material for the sample-holding portions while changing the printing times for each sample-holding portion (i.e., variously changing the number of printing operations for a single sample-holding portion).

Alternatively, the sample-holding portions of the test instrument of the present invention may be designed such that each portion comprises a region for absorbing the sample and a region for inclusion of the foregoing reagent in advance (i.e., a reagent-containing region) so that these regions serve as one sample-holding portion when the sample is added to these regions upon practical use.

In this case, the sample-holding portion can, for instance, be prepared by forming the region for absorbing the sample on the base through a printing operation using an ink which comprises a water-absorbing gel, a binder and a solvent or a dispersion medium and then forming the reagent-containing region on the sample-absorbing region previously formed in a pattern almost identical to that of the latter through a printing operation using, for instance, an ink which comprises a reagent, a binder and a solvent or a dispersion medium to thus laminate these two regions. These sample-absorbing region and the reagent-containing region may be applied onto the base in the reverse order.

Figure 4:
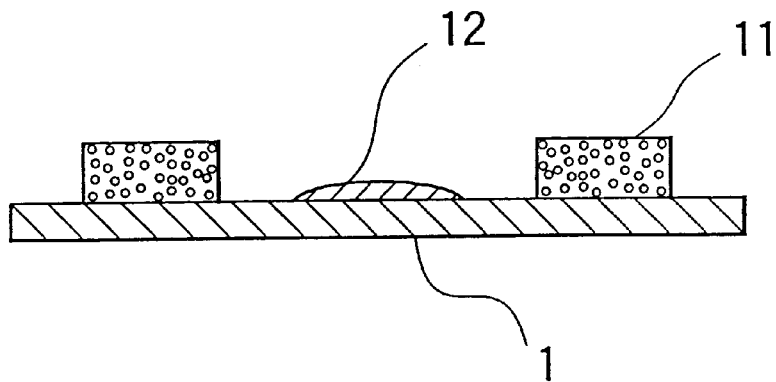
FIG. 4 is a schematic cross sectional view of a sample-holding portion of the test instrument of the present invention, which is designed such that the sample-holding portion comprises portions for absorbing the sample and portions for containing the sample.
Figure 5:
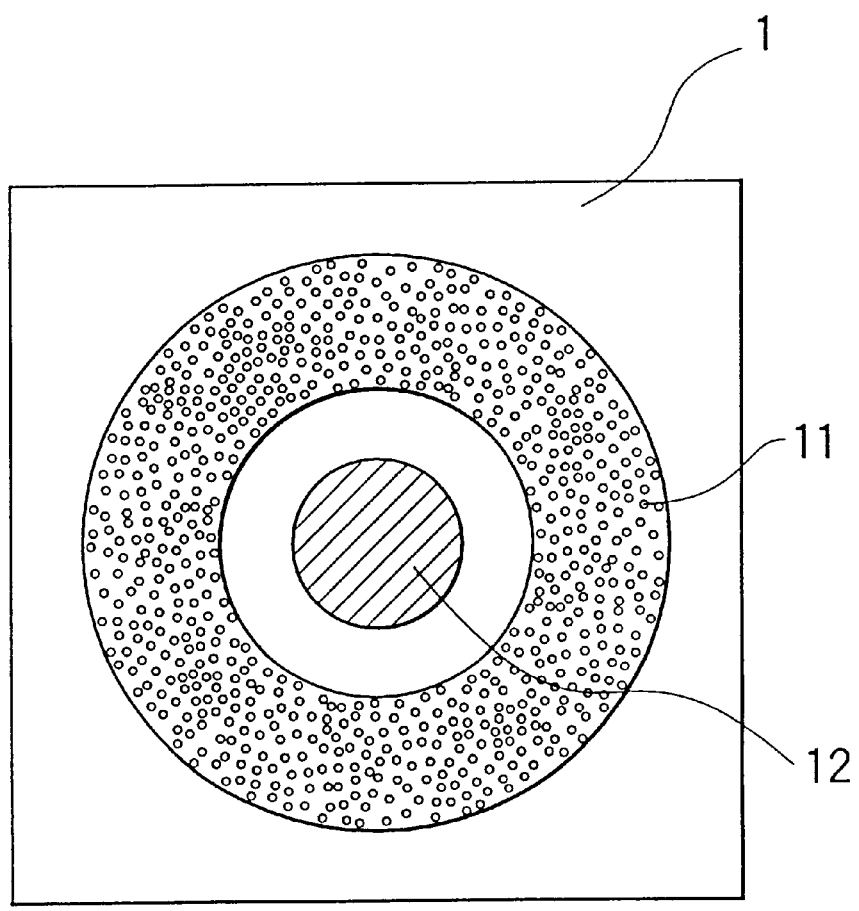
FIG. 5 is a schematic plan view of the sample-holding portion as shown in FIG. 4.

The sample-holding portion of the test instrument of the present invention may comprise, for instance, two regions independently formed on the base, i.e., a reagent-containing region 12 and a sample-absorbing region 11 surrounding the region 12, whose cross sectional and plan views are shopwn in FIGS. 4 and 5 respectively. If the sample-holding portion has such a construction, the material for forming the sample-absorbing region should be selected from those capable of sufficiently expanded through absorption of water so that the sample-absorbing region gets swollen upon addition of a sample and that the former thus cover the reagent-containing region to unite these two regions and to thus ensure the distribution of the reagent throughout the region. Preferred examples of such materials are a variety of water-absorbing gels listed above.

Figure 6:
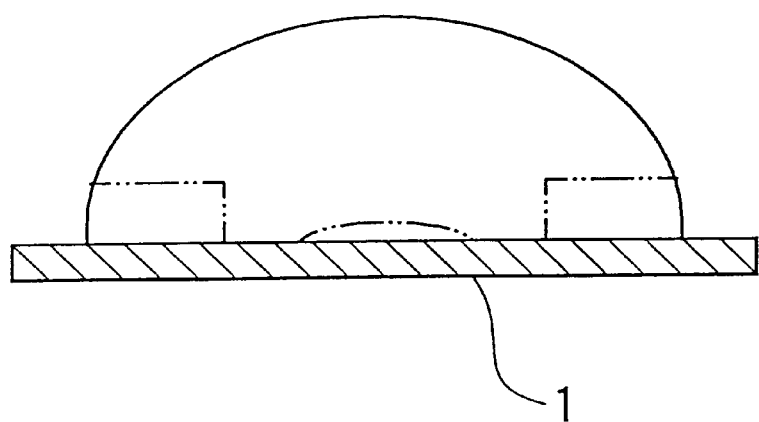
FIG. 6 is a schematic cross sectional view showing an example of the sample-holding portion having the shape as shown in FIG. 4 to which a sample is added.

When the sample-holding portions having a shape as shown in FIGS. 4 and 5 using a water-absorbing gel, the addition of a sample causes expansion of the water-absorbing gel present in the sample-absorbing region, whose cross sectional view is shown in FIG. 6, and these two regions serve as a single sample-holding portion.

When forming the sample-holding portion so as to have the foregoing construction, the sample-absorbing region and the reagent-containing region may come in contact with one another or may be separated from one another at a certain distance inasmuch as these two regions are united when a sample is added thereto.

Figure 7:
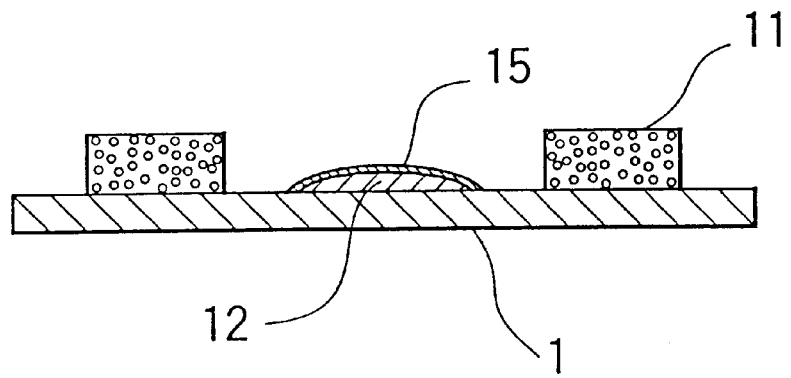
FIG. 7 is a schematic cross sectional view showing another example of the sample-holding portion as shown in FIG. 4.

Moreover, if forming the sample-holding portion so as to have the construction as shown in FIG. 4, a protective layer 15 comprising a polymer such as those listed above may be formed on the reagent-containing region as shown in FIG. 7 in order to prevent any reagent from falling off.

In case where the sample-absorbing region and the reagent-containing region are separately formed as has been discussed above, the sample-holding portions which are required for the aforementioned test instrument used in the determination of the sensitivity of bacteria to antibacterial agents and in which the amount of a reagent is not identical, but the amount of the sample to be retained is identical can easily be produced by forming the sample-absorbing region from a constant amount of a water-absorbing gel and a binder, forming the reagent-containing region through a printing operation using an ink which comprises a reagent and a binder, while changing the amount of the ink containing the foregoing reagent by changing the amount of the ink transferred through the control of the depth or the number of lines on the printing plate or by changing the concentration of the reagent, during the printing operation.

The liquid-absorbent body used in the test instrument of the present invention is selected from materials which can relatively rapidly absorb an aqueous liquid when coming in contact with the liquid, but when pouring a liquid sample in the sample container at the usual speed, they can absorb the liquid sample at such a velocity that the inner bottom face of the container on which the sample-holding portions are formed is once covered with the liquid sample. This is because, if the liquid-absorbing speed of the liquid-absorbent body is too fast, the sample is absorbed by the absorbent body prior to the complete distribution of the sample throughout the bottom face of the sample container. Accordingly, the sample does not come in contact with the sample-holding portions at all and the foregoing method may often fail in the retention of the sample on the sample-holding portions. For this reason, if the majority of the inner face of the sample container which comes in contact with the sample is constituted by the liquid-absorbent body, any material showing such an extremely high absorbing speed cannot be used. In this regard, however, the overall absorbing speed of such a material having an extremely high absorbing speed may be controlled by reducing the area which comes in contact with the liquid sample. For instance, the whole face of the sample container which comes in contact with the liquid sample may be formed from a material such as those used for forming the base, followed by forming small holes at any position on the face which comes in contact with the liquid sample and then forming the liquid-absorbent body in such a manner that the body is exposed through the holes.

Examples of materials used for forming the liquid-absorbent body of the present invention include (1) filter paper, water-absorbing paper, nonwoven fabrics, polymeric fibers such as acetate filaments, fibrous materials having water-absorbing and water retention characteristics such as cottom fibers, e.g., those available from Kanebo, Ltd. under the trade name of BELLOASIS; (2) sponge-like porous bodies comprising a variety of polymers; (3) water-absorbing gels, for instance, polyvinyl alcohol/polyacrylate type gels, cross-linked polyacrylate type gels, cross-linked polyvinyl alcohol type gels, cross-linked polyethylene oxide type gels, cross-linked polyacrylamide type gels such as cross-linked polydiethyl acrylamide gels and cross-linked polyisopropyl acrylamide gels, cross-linked polyvinyl pyrrolidone type gels and cross-linked PAOGEN (trade mark) gels, which may be used alone or in any combination thereof; (4) water-absorbing sheets obtained by sandwiching the foregoing water-absorbing gel between, for instance, nonwoven fabrics and/or paper such as water-absorbing sheets distributed under the trade name of AQUAKEEPER (Sumitomo Seika Chemicals Co., Ltd.) and DRIPSHEET (Dai Nippon Printing Co., Ltd.); (5) water-absorbing sheets in which the materials listed above in connection with (1), (2) and (4) and the foregoing water-absorbing gel coexist, such as those comprising paper and powdery water-absorbing gel sprayed thereon; (6) water-absorbing sheets prepared by coating a base such as a polymer sheet of, for instance, polyethylene, polypropylene, ethylene-vinyl acetate copolymer, ethylene-vinyl alcohol copolymer, polystyrene, polyacrylate, polyvinyl chloride, polyvinyl alcohol, polyvinyl butyral, polyamide, polyester, polycarbonate, polyurethane, polyimide or triacetyl cellulose, paper or a nonwoven fabric with the foregoing water-absorbing gel in combination with a binder, for instance, hydrophobic resins (water-insoluble resins) such as acrylic resins, e.g., those commercially available from Mitsubishi Rayon Co., Ltd. under the trade mark "Dianal" BR-Resin, polyvinyl butyral, polyester resins, polyurethane resins, fluoroplastics, silicone resins and styrene-butadiene latex resins, and resins soluble in water and simultaneously soluble in organic solvents (soluble in both aqueous and organic solvents) such as polyvinyl pyrrolidone and hydroxypropyl cellulose (these binders may likewise be use alone or in any combination thereof); (7) water-absorbing sheets prepared by coating a base such as those described above with a material which is soluble in organic solvents and capable of getting swollen obtained by, for instance, partially cross-linking a polyethylene glycol such as those commercially available from Sumitomo Seika Chemicals Co., Ltd. under the trade name of AQUACOKE or a variety of water-soluble polymer such as polyacrylamide, poly(sodium acrylate), polyethylene oxide, polypropylene oxide, polyvinyl alcohol and polyvinyl pyrrolidone, followed by irradiating with ionizing radiation to thus make the coated layer insoluble in water; and (8) any combination of the foregoing materials (1) to (7). The liquid-absorbent body having any pattern can be formed on the base by the printing method like the foregoing sample-holding portions if using, in particular, the materials (6) and (7) listed above.

The liquid-absorbent body composed of these materials is formed in an amount sufficient for removing, through absorption, the excess of the liquid accommodated in the sample container except for that to be retained in the sample-holding portions.

In specific examples according to the first embodiment of the present invention shown in FIGS. 1 to 3, the test instrument of the present invention comprises a base provided thereon with sample-holding portions and a liquid-absorbent body arranged on the base, the inner bottom face of the sample container for accommodating a liquid sample is defined by the face of the base to which the sample-holding portions are fitted and the inner side of the container is defined by the foregoing liquid-absorbent body. The test instrument having such a construction according to the present invention is preferred from the viewpoint of the production thereof, since it can easily be prepared by arranging and fixing the liquid-absorbent body in such a manner that the sample container is formed on the base. In this case, the outer surface of the liquid-absorbent body which does not come in direct contact with the liquid sample may be covered with a different water-impermeable material 4 in order to prevent any scattering of the sample absorbed by the liquid-absorbent body and to simplify the handling of the resulting test instrument easy. Such a water-impermeable material used for covering the liquid-absorbent body may be those listed above for forming the base. These base and coated portion of the liquid-absorbent body may integrally be formed from an injection-moldable material.

Figure 8:
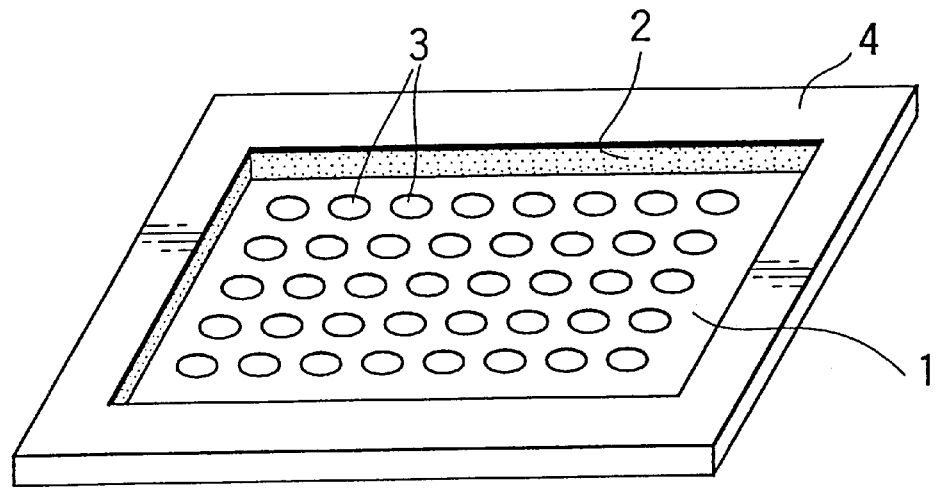
FIG. 8 is a perspective view schematically illustrating the instrument for tests according to a second embodiment of the present invention.
Figure 9:
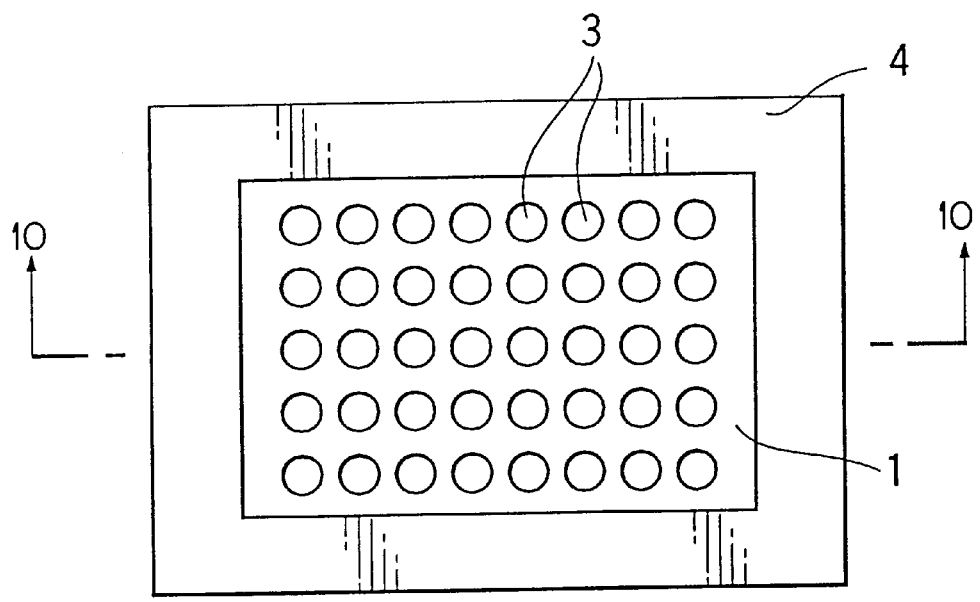
FIG. 9 is a top plan view showing the test instrument as shown in FIG. 8.

FIG. 8 is a perspective view illustrating the test instrument according to a second embodiment of the present invention; FIG. 9 is a top plan view of the test instrument as shown in FIG. 8; and FIG. 10 is a cross sectional view of the test instrument as shown in FIG. 9, taken along the line BB'.

Figure 10:
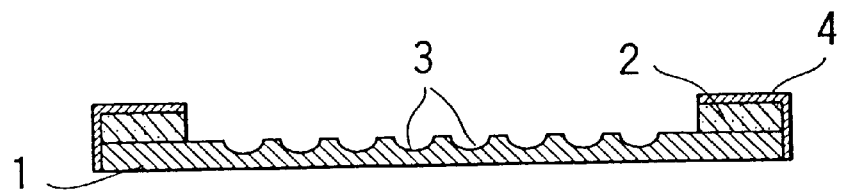
FIG. 10 is a cross sectional view of the test instrument as shown in FIG. 9, taken along the line BB' in FIG. 9.

In the second embodiment of the present invention as shown in FIGS. 8 to 10, the sample-holding portions 3 are formed as concave portions arranged on the bottom of the container. The other construction may be the same as those disclosed in FIG. 1.

In this embodiment, if the liquid sample once accommodated in the sample container is removed by the liquid-absorbent body through absorption like the foregoing first embodiment, the sample is accommodated in the concave portion and retained in the swollen condition due to its surface tension. Therefore, the inner face of the concave portion of the sample-holding portion must not particularly be hydrophilic. However, the bottom face of the sample container other than the sample-holding portions must be hydrophobic (or water-repellent) in nature to thus ensure sufficient removal of the excess liquid sample.

The shape of the concave portion of the sample-holding portion is not restricted to any specific one in this embodiment and may be a concave portion composed of a curved surface such as those observed for the usual microplate or a cylindrical or conical concaved portion.

The size of the sample-holding portion in this embodiment must be such that a desired amount of a sample may be retained in the portions after removing the excess sample liquid through absorption by the liquid-absorbent body. The specific size thereof is not restricted to a particular range inasmuch as the foregoing requirements are satisfied, but preferred are those having a diameter ranging from 3 to 10 mm and a depth ranging from 0.5 to 5 mm and capable of holding a sample in an amount ranging from about 0.01 to 0.2 ml.

Figure 11:
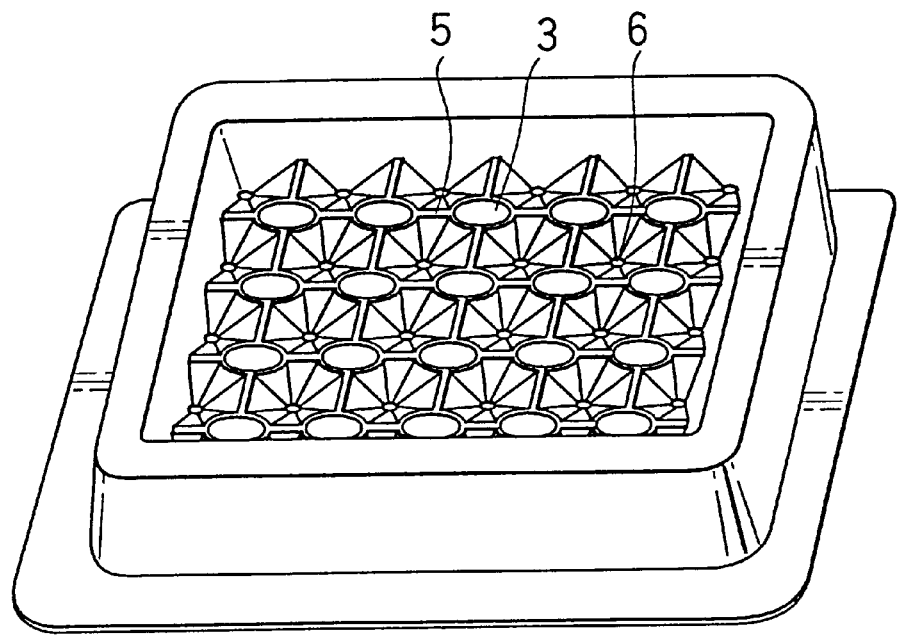
FIG. 11 is a perspective view schematically illustrating the instrument for tests according to a third embodiment of the present invention.
Figure 12:
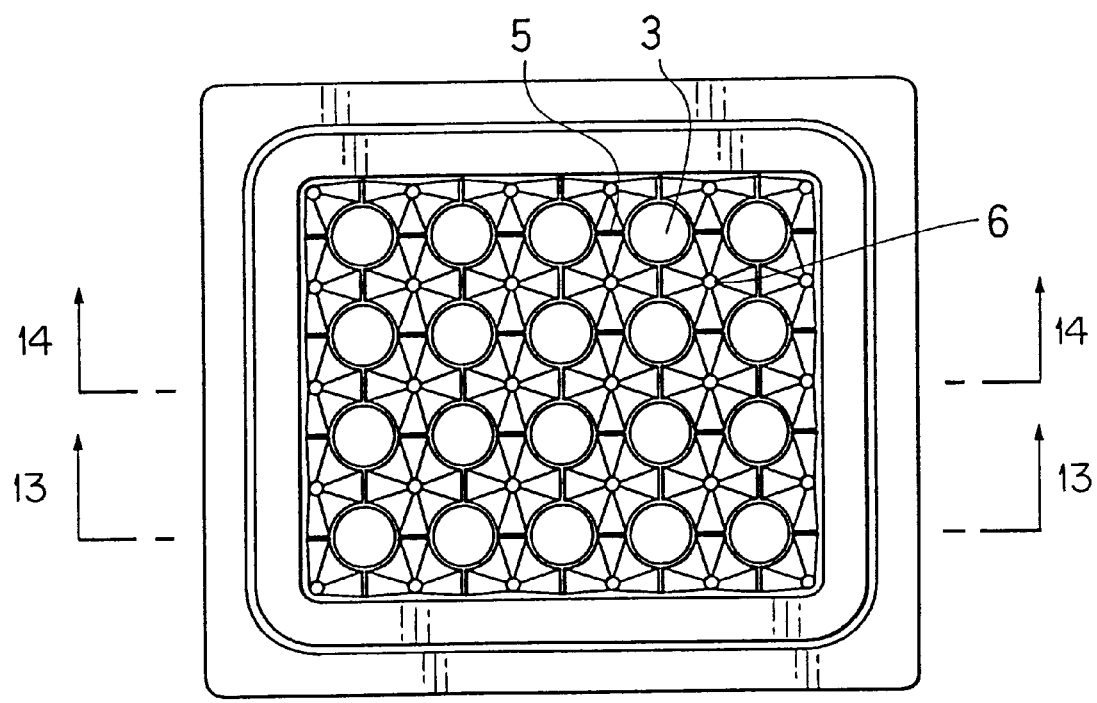
FIG. 12 is a top plan view showing the test instrument as shown in FIG. 11.
Figure 13:
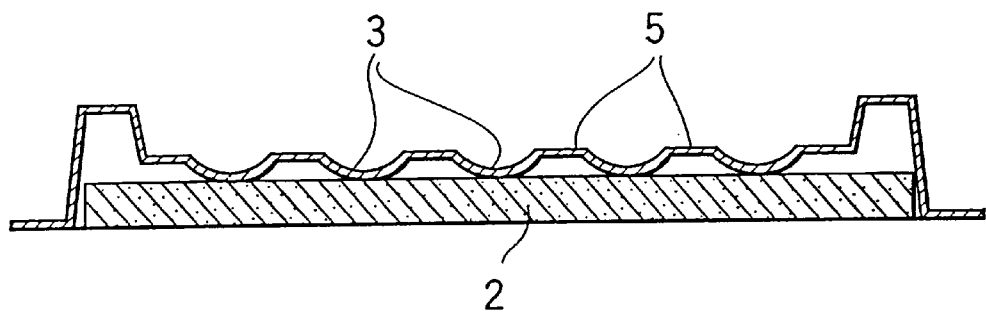
FIG. 13 is a cross sectional view of the test instrument as shown in FIG. 11, taken along the line CC' in FIG. 12.
Figure 14:
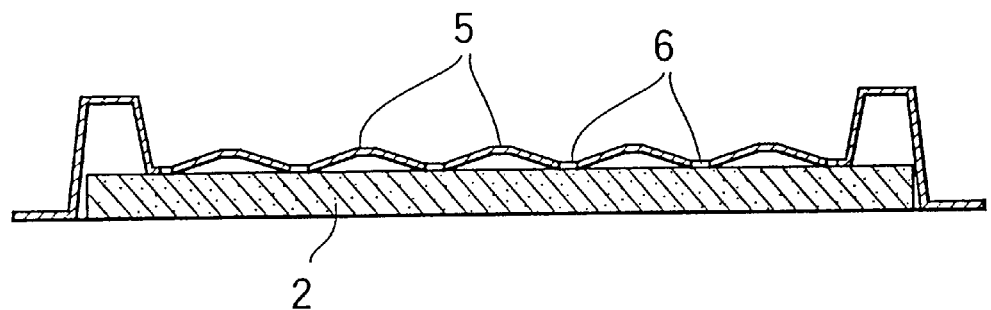
FIG. 14 is a cross sectional view of the test instrument as shown in FIG. 11, taken along the line DD' in FIG. 12.

FIG. 11 a perspective view of the test instrument according to a third embodiment of the present invention; FIG. 12 is a top plan view of the test instrument as shown in FIG. 11; FIG. 13 is a cross sectional view of the test instrument as shown in FIG. 12, taken along the line CC'; and FIG. 14 is a cross sectional view of the test instrument as shown in FIG. 12, taken along the line DD'.

In the third embodiment of the present invention as shown in FIGS. 11 to 14, the sample-holding portions 3 are designed such that the periphery thereof is higher than the level of the bottom of the container except for the sample-holding portions. In other words, the bottom face of the sample container other than the sample-holding portions is lower than the external edge of the sample-holding portions. If the sample-holding portion has such a structure, the liquid sample once accommodated in the sample container is absorbed by the liquid-absorbent body to thus lower the liquid level and when the liquid level is reduced to a level of lower than the external edge portion of the sample-holding portions, the excess sample floods the bottom face of the container other than the sample-holding portions and is removed therethrough. Thus, a desired amount of the sample can certainly be retained in the sample-holding portions.

Therefore, the whole of the bottom face of the sample container other than the sample-holding portions must not strictly be lower than the peripheral edge of the sample-holding portions and the levels of portions distant apart from the sample-holding portions, linear portions for connecting the sample-holding portions and substantially free of any width or the like may be identical to or higher than that of the peripheral edge of the sample-holding portions inasmuch as the instrument can ensure the foregoing functions. In the specific examples as shown in FIGS. 11 to 14, the linear portions 5 for connecting the sample-holding portions and substantially free of any width is positioned at the level identical to that of the peripheral edge of the sample-holding portions.

The sample-holding portions in this embodiment may be hydrophilic regions like the foregoing first embodiment or concave regions like the second embodiment, but preferred are concave regions, as in the specific example shown in FIGS. 11 to 14, whose external edge corresponds to the highest portions of the bottom face of the sample container.

Furthermore, the sample-holding portions each preferably has such a construction that the center of the part positioned between every neighboring two sample-holding portions is the lowest part as shown in FIGS. 11 to 14. Moreover, it is preferred that the sample-holding portions be designed in such a manner that the liquid-absorbent body 2 is brought into contact with the liquid sample accommodated in the sample container at that lowest part 6. In the specific embodiment shown in FIGS. 11 to 14, the liquid-absorbent body is positioned below the sample container, while holes are formed through the lowest central part situating between the sample-holding portions on the bottom of the sample container, the liquid-absorbent body is exposed to the inner face of the sample container through the holes and thus the liquid-absorbent body comes in contact with the liquid sample when the liquid sample is accommodated in the sample container.

If the sample-holding portions are designed to have such a construction, all of the excess liquid sample flows down to the central lowest part situating between every neighboring two sample-holding portions and is absorbed at that part by the liquid-absorbent body and therefore, the test instrument of the invention can ensure efficient removal of the excess liquid sample. Moreover, the sample-holding portions are preferably formed as concave portions, since the sample-holding portions and the sample container may integrally be formed from the foregoing materials such as plastic sheets, in such case.

Figure 15:
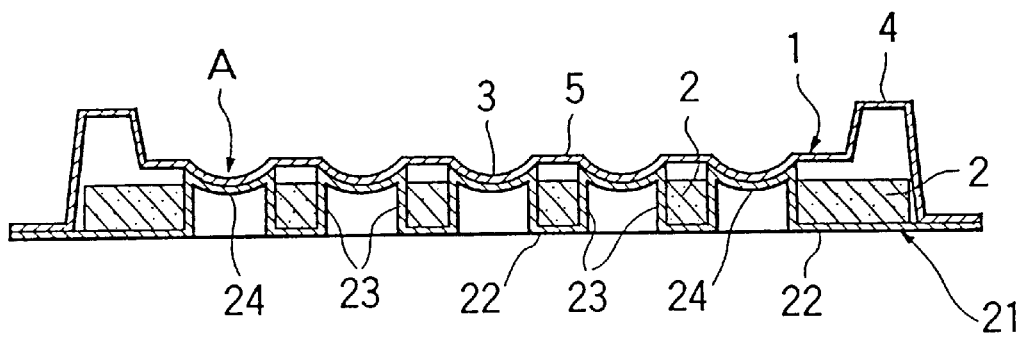
FIG. 15 is a cross sectional view showing a variation of the instrument for tests according to the third embodiment, taken along the line CC' in FIG. 11.

FIG. 15 is a cross sectional view of a variation of the test instrument according to the foregoing third embodiment and FIG. 15 shows a longitudinal cross sectional view of the test instrument taken along the line CC' in FIG. 12.

In FIG. 15, the sample container constituting the test instrument is provided with a base 1 having the structure as shown in FIGS. 11 to 12 and an absorbent body-accommodating tool 21 positioned below the base 1. The base 1 comprises, as shown in FIGS. 11 to 12, a plurality of sample-holding portions 3; linear portions 5 each arranged while connecting the sample-holding portions to one another and low level parts 6 arranged within the region surrounded by the linear portions 5. Moreover, the absorbent body-accommodating tool 21 comprises a plate-like body 22 which forms a flat bottom wall; cylindrical standing-up walls 23 upwardly extending from the plate-like body 22; and concave top walls 24 for closing the top portions of the standing-up walls 23.

The outer contour of the plate-like body 22 is substantially in agreement with that of the base 1 and the plate-like body 22 and the base 1 form an absorbent body-accommodating space which is substantially closed except for the hole (see FIG. 12) formed at the low level part 6. The standing-up wall 23 is positioned immediately below the sample-holding portion 3, the cross sectional contour of the standing-up wall 23 is substantially in agreement with the outer peripheral contour of the sample-holding portion 3 and the upper face of the concave top wall 24 and the lower face of the sample-holding portion 3 are complementary to one another in shape. The liquid-absorbent body 2 having such a height (thickness) that the body substantially reaches the lower face of the low level part 6 is arranged around the standing-up wall 23. Accordingly, the liquid-absorbent body 2 is positioned immediately below the low level part 6 and the upper face of the liquid-absorbent body 2 comes close to the hole of the low level part 6.

It is preferred to form the base 1 and the absorbent body-accommodating tool 21 from a transparent material, since the degree of color development of the sample-holding portions 3 after the test can automatically and easily be determined by making light rays incident upon them from the direction A.

Figure 16:
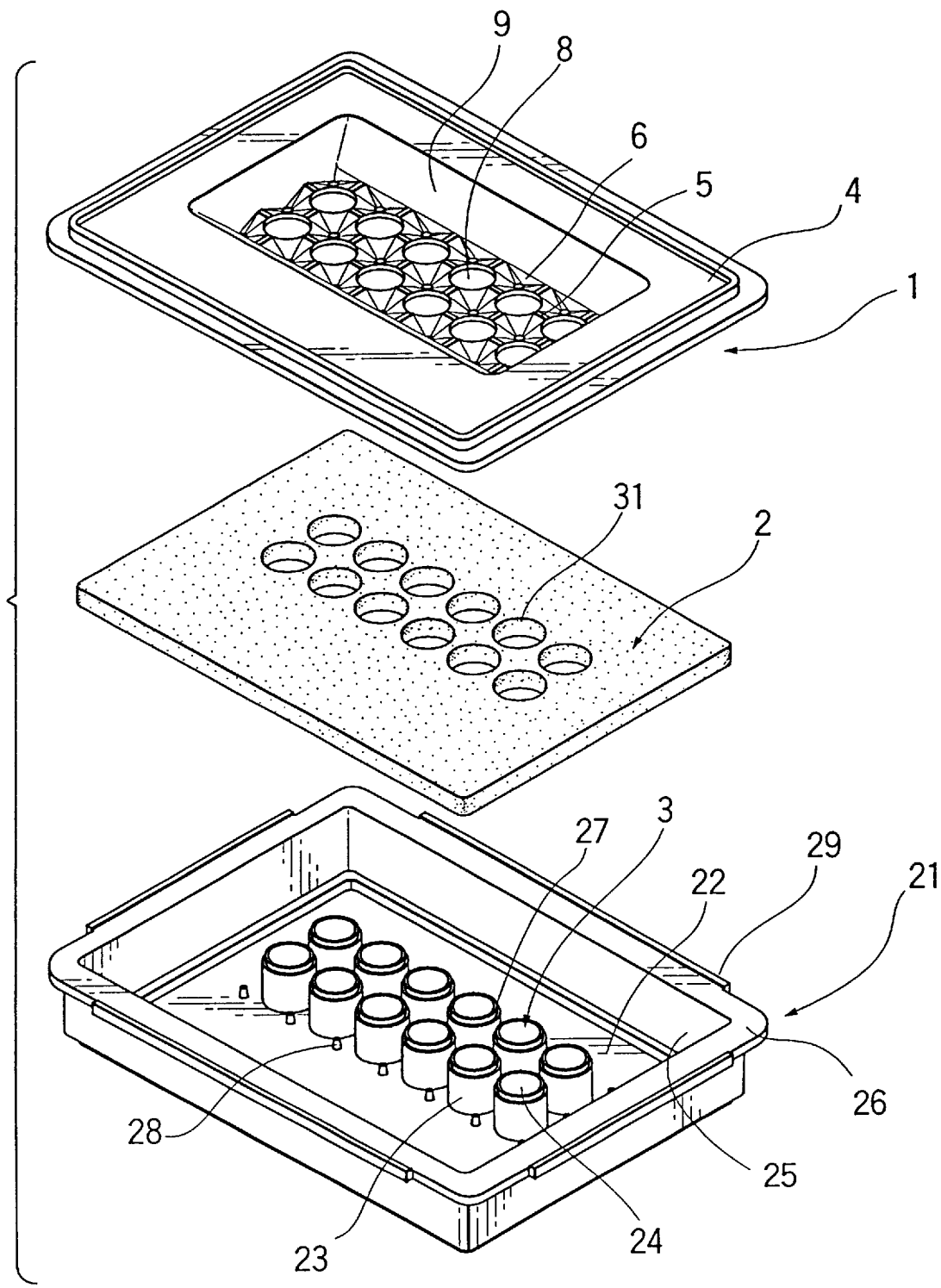
FIG. 16 is an exploded perspective view showing another variation of the test instrument according to the third embodiment.
Figure 17:
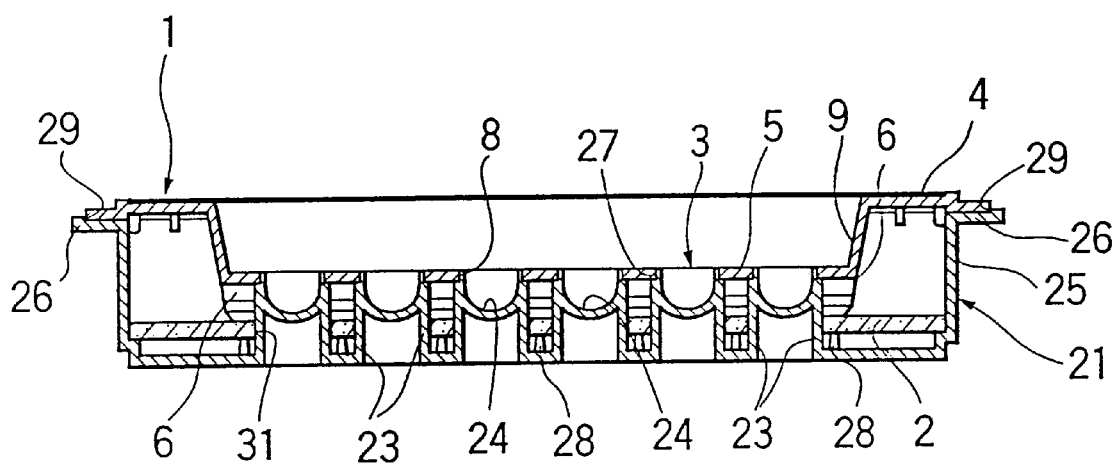
FIG. 17 is a longitudinal cross sectional view of the test instrument as shown in FIG. 16.

FIG. 16 is an exploded perspective view showing another variation of the test instrument of the present invention according to the third embodiment and FIG. 17 is a cross sectional view of the test instrument as shown in FIG. 16.

The test instrument as shown in FIG. 16 comprises a base 1 which constitutes the bottom face of a sample container; a liquid-absorbent body 2 arranged on the lower side of the base 1; and an absorbent body-accommodating tool 21 capable of accommodating the liquid-absorbent body 2 therein. A concave portion is formed by a downward curved continuous wall 9 in the central region of the base 1 and a plurality of circular openings 8 are arranged at desired distances on the bottom of the concave portion. Linear portions 5 extending in the direction of the diameter of the opening 8 are arranged so that the peripheral edges of the openings 8 are connected to one another and each linear portion 5 extends between every two neighboring openings 8 on the plane (or at the height) on which the peripheral edge of the openings 8 are positioned. The bottom face of the base 1 downward extends at an angle within the region surrounded by the periphery of the openings 8 and the linear portions 5 to thus form a funnel-like low level part 6. A hole or opening is formed at the center of the lower most low level part 6 and it permits the liquid communication of the upper region with the lower region of the base 1.

The liquid-absorbent body 2 has an outer contour capable of being accommodated in the absorbent body-accommodating tool 21 and is provided with, at the center thereof, through-holes 31 the number of which is identical to that of the circular openings 8 on the base 1. Each through-hole 31 has a circular cross section having a diameter slightly larger than that of the circular opening 8 and formed through the liquid-absorbent body 2 at distances substantially identical to those observed for the circular opening 8. The absorbent body-accommodating tool 21 which is, as a whole, formed in a container having an opened top is provided with a bottom wall 22, an external peripheral wall 25 and external edges 26. A linear step portion 29 which can be aligned with the outer periphery of the base 1 is formed at each external peripheral edge 26. Moreover, the cylindrical standing-up walls 23 are formed at the center of the bottom wall 22 and the number thereof is identical to that of the circular openings 8 or the through-holes 31. The outer diameter of the standing-up wall 23 is substantially in agreement with the inner diameter of the through-hole 31. The top of the standing-up wall 23 is closed by a downward depressed-concave top wall 24 and the upper face of the top wall 24 forms concave sample-holding portion 3. A step portion 27 in the circumferential direction is formed at the upper outer periphery of the standing-up wall 23 and the outer diameter of the tapered portion (upper portion) of the step portion 27 is substantially consistent with the inner diameter of the opening 8 of the base 1.

When practically using the test instrument, the liquid-absorbent body 2 is accommodated in the absorbent body-accommodating tool 21 as shown in FIG. 17, each cylindrical standing-up wall 23 of the absorbent body-accommodating tool 21 passes through each circular through-hole 31 of the liquid-absorbent body 2. In addition, the base 1 is put on the absorbent body-accommodating tool 21 like the cap for the tool 21 and the external peripheral edge of the base 1 is mounted on the external peripheral edge 26 of the tool 21. Each circular opening 8 of the base 1 is aligned with the top of each standing-up wall 23 of the tool 21. As shown in FIG. 17, the stepped portion 27 of the standing-up wall 23 is fitted to the opening 8 of the base 1 and the outer peripheral top edge of the standing-up wall 23 is set in the prescribed position on the plane identical to the bottom plane of the sample container.

Moreover, the height (thickness) of the liquid-absorbent body 2 is set at a level at which the upper plane of the liquid-absorbent body 2 comes close to the hole formed at the lower most part of the funnel-like low level part 6. In the embodiment shown in FIGS. 16 and 17, a plurality of projections 28 are arranged in the vicinity of each standing-up wall 23. Each projection 28 is set in the prescribed position, i.e., immediately below the hole of each low level part 6 so that the liquid-absorbent body 2 is certainly positioned in the vicinity of the hole of the low level part 6.

In this variation, it is also preferred to form the base 1 and the absorbent body-accommodating tool 21 from a transparent material, since the degree of color development of the sample-holding portions 3 after the test can automatically and easily be determined by making light rays incident upon them from the direction A and this is also effective to efficiently eliminate any influence, upon the transmittance of the light rays incident thereupon from the direction A, of the water vapor adhered to the interstice between the concave top wall 24 and the sample-holding portion 3 as in the variation shown in FIG. 15.

In the forth embodiment of the test instrument of the present invention, the instrument is provided with a cap body for the sample container, the liquid-absorbent body is fitted to the cap body and a liquid sample is poured into the sample container. Thus, the liquid-absorbent body comes in contact with the liquid sample when the cap body is fitted to the sample container to absorb the excess sample other than the sample to be retained in the sample-holding portions. In this embodiment, the shapes of the cap body and the liquid-absorbent body are not restricted to any specific ones so far as the test instrument ensures the foregoing functions, but the instrument is preferably designed in such a manner that the liquid-absorbent body comes in contact with the sample in the portion other than the portion situating just above the sample-holding portions. Thus, a desired amount of the sample is held in the sample-holding portions.

Figure 18:
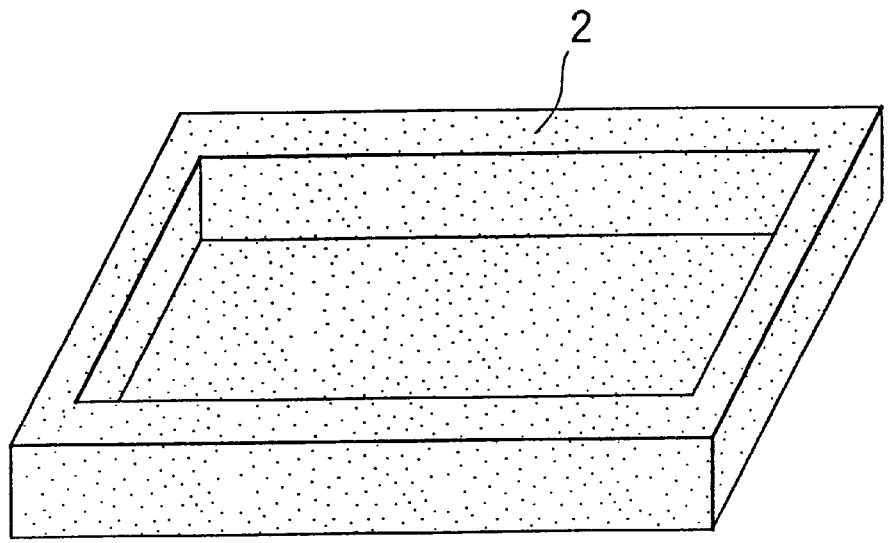
FIG. 18 is a perspective view showwing an example of the liquid-absorbent body used in the test instrument of the present invention according to a forth embodiment.
Figure 19:
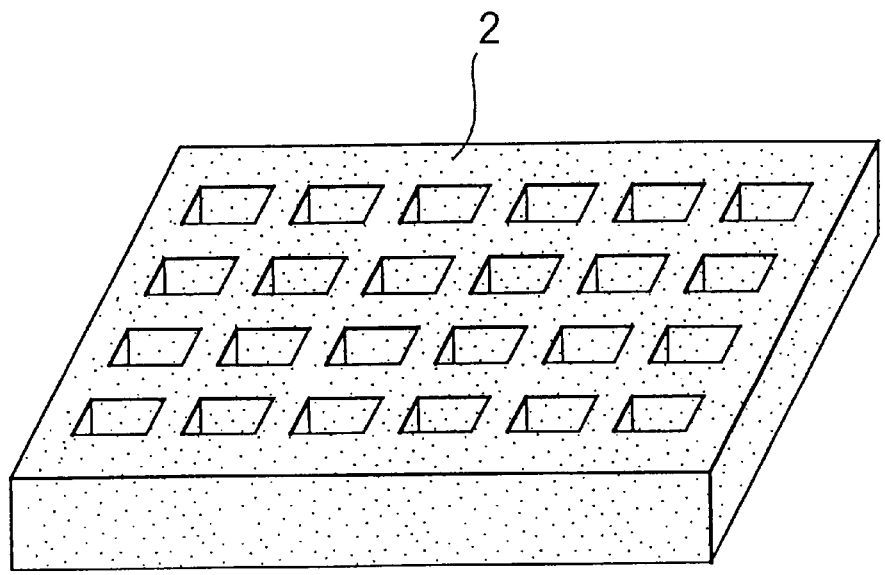
FIG. 19 is a perspective view showing another example of the liquid-absorbent body used in the test instrument of the present invention according to the forth embodiment.

FIGS. 18 and 19 show examples of such liquid-absorbent bodies usable in the test instruments of the present invention according to such an embodiment.

The liquid-absorbent body as shown in FIG. 18 is slightly smaller than the sample container and has a rectangular outer shape so that the body can be inserted into the sample container, the part corresponding to the portion on the bottom face of the sample container on which the sample-holding portions are formed is in the form of a rectangular cavity smaller than the outer shape, and it is designed to have such a structure that, when a cap body is fitted thereto and the cap body is in turn fitted to the sample container, the bottom face of the liquid-absorbent body approximately comes in contact with the bottom of the sample container at the outer periphery of the portion on the bottom face of the sample container on which the sample-holding portions are formed.

The liquid-absorbent body shown in FIG. 19 has an outer shape and the overall size identical to those shown in FIG. 15, but the part corresponding to the portion on the bottom face of the sample container on which the sample-holding portions are formed independently forms a cavity and it is designed in such a manner that, when a cap body is fitted thereto and the cap body is in turn fitted to the sample container, the liquid-absorbent body approximately comes in contact with the bottom of the sample container at the outer periphery of the portion on the bottom face of the sample container on which the sample-holding portions are formed and the portions situating between every two neighboring sample-holding portions.

Figure 20:
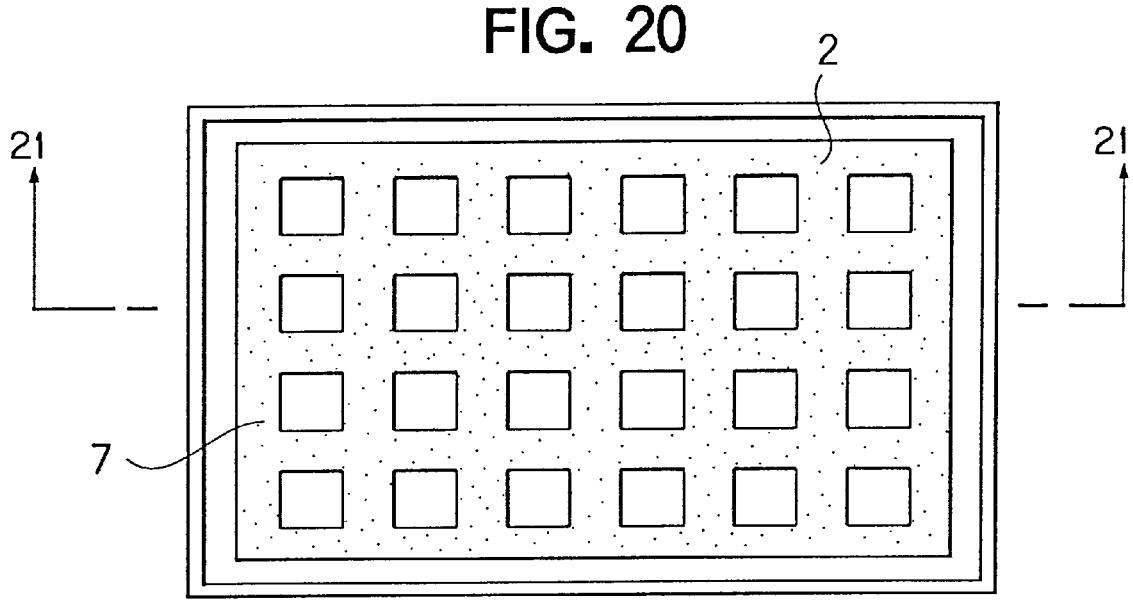
FIG. 20 is a bottom plan view of a cap body used in the test instrument, to which the liquid-absorbent body as shown in FIG. 19 is fitted, of the present invention according to the forth embodiment.
Figure 21:
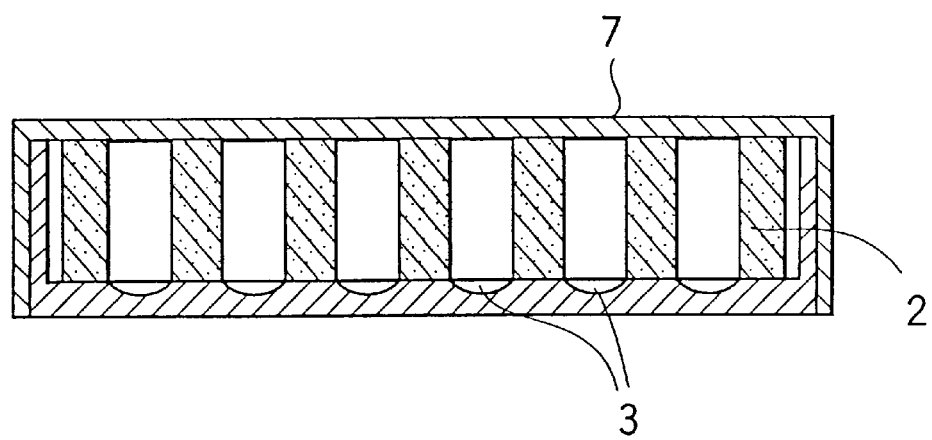
FIG. 21 is a cross sectional view of the test instrument according to the 4th embodiment of the present invention, to which the cap body as shown in FIG. 20 is fitted to the sample container, taken along the line corresponding to the line EE' in FIG. 20.

FIG. 17 is a bottom view of a cap body 7 to which the liquid-absorbent body shown in FIG. 19 is fitted and FIG. 21 shows a cross sectional view of the sample container to which the cap body shown in FIG. 20 is fitted, at the position corresponding to the line EE' in FIG. 20.

In the test instrument of the present invention according to the forth embodiment, the sample container does not comprise any liquid-absorbent body and therefore, a part of the inner wall of the sample container is not constituted by the liquid-absorbent body unlike the foregoing first to third embodiments. The other constructions such as the structure of the sample-holding portions may be the same as those discussed above in connection with the foregoing first to third embodiments.

When using the foregoing test instrument of the present invention, a desired reaction solution or culture medium is added to the sample-holding portions of the instrument to thus carry out a reaction or cultivation, followed by, if necessary, addition of a reagent required after the reaction or the cultivation and detection of the test results on the basis of, for instance, the color development, light emission, emission of fluorescent rays or changes in turbidity, depending on the principle of each test.

For instance, when determining the lowest inhibitory concentration of an antibacterial agent, there have been known, for instance, a method for visually detecting the proliferation of bacterial in the culture medium; a method for detecting the turbidity of the culture medium by means of the absorbance observed at 500 to 700 nm; and a method which comprises the steps of adding a fluorescent substrate to the culture medium, determining the amount of a fluorescent substance generated by the action of the bacterial enzyme accumulated in the culture medium as the proliferation of the bacteria proceeds through the determination of the intensity of the fluorescent rays emitted by the substance and determining the correlation between the proliferation of the bacteria and the intensity of the fluorescent rays.

The addition of, for instance, a reaction solution or a culture medium to the sample-holding portions can be carried out by simply injecting an appropriate amount (the amount sufficient for completely soaking at least the sample-holding portions) of the same into the sample container using, for instance, a pipette. Thus, a desired amount of the sample can be retained in the sample-holding portions.

In order to retain a sample in each sample-holding portion in the foregoing test instrument according to the forth embodiment, the sample is poured into the sample container to such an extent that at least the sample-holding portions on the bottom of the container are soaked, thereafter a cap body is fitted to the container. Then the cap body is removed after the excess sample is absorbed by the liquid-absorbent body and a desired amount of the sample is retained in the sample-holding portions.

Test results are most simply detected with the naked eyes, but if more correct results are required or if the results cannot be observed with the naked eyes, in particular, the sample-holding portions are very small, the turbidity, the developed color, the emitted light, the generated fluorescent rays or the like listed above can be detected by any conventionally used detection device to thus give desired test results. The measurement of, for instance, absorbance and intensity of fluorescent rays for the determination of the foregoing minimum inhibitory concentration of an antibacterial agent can be carried out using any commercially available absorption spectrophotometer or fluorometer. The test instrument of the present invention may be produced so as to be adapted to these automated known measuring instruments.

The test instrument of the present invention can be used in a variety of chemical tests which make use of biological substances such as antigens, antibodies and/or enzymes, and/or non-biological substances such as color-developing compounds and microbiological tests including cultivation of microorganisms, which have conventionally been carried out using microplates of plastics and the instrument of the invention can quite easily and rapidly form a large number of reaction systems without dispensation thereof by, for instance, a micropipette. Moreover, any scatter of the sample in the surroundings during the test can effectively be prevented.

The present invention will hereinafter be explained in more detail with reference to Examples, but the present invention is not limited to these specific Examples at all. In the following Examples, the term "%" means "% by weight".

EXAMPLE 1

Test Instrument According to the 1st Embodiment of the Present Invention

The test instrument according to the first embodiment of the present invention, as shown in FIGS. 1 to 3, was produced by the method detailed below.

A pattern of circular solids [6(lengthwise)×10 (widthwise)], each having a diameter of 5 mm and a thickness (as determined after drying) of 25 $\mu$m, was printed on a polyethylene terephthalate sheet having a length of 6 cm, a width of 10 cm and a thickness of 100 $\mu$m and having a tackiness-imparted back face by the screen printing method which made use of a 10% aqueous solution of a water-soluble polyacrylamide resin (available from Wako Pure Chemical Co., Ltd.), followed by drying and irradiation with 10 Mrad of an electron beam (EB) at an accelerating voltage of 180 kV using an electron beam irradiation apparatus (Curetron, available from Nisshin High Voltage Co., Ltd.) to thus form a water-absorbing gel layer.

Then 6 kinds of antibacterial agents were coated on the pattern of these circular solids at 9 different concentrations and the remaining one rank was defined to be controls free of any antibacterial agent. Specific antibacterial agents used are listed in the following Table 1, a 1% Hydroxypropyl Cellulose (HPC) Type-L (available from Nippon Soda Co., Ltd.) in isopropyl alcohol containing each antibacterial agent was used as an ink, 0.01 ml each of the solution was applied to the corresponding circular solid using a dispenser and then dried. The content of each antibacterial agent present in the solution was changed in such a manner that the coated amount of PVP was identical, while the content of the antibacterial agent was adjusted to 160, 80, 40, 20, 10, 5, 2.5 or 1.25 ng for each antibacterial agent. Further a protective film was formed thereon by dropwise adding a 5% solution of HPC Type-L in isopropyl alcohol (0.01 ml each) thereto using a dispenser and then drying. Moreover, As a control, a HPC solution free of any antibacterial agent was also applied to one rank of the circular solid.

A test instrument was produced by forming a polystyrene container which comprised a base having a length of 8 cm and a width of 12 cm and a liquid-absorbent body-covering member 4 having a height of 0.8 cm and a width of 1 cm through integral injection-molding, filling the space formed between the base and the covering member with acetate filament fibers (3 g in all) as the liquid-absorbent body and then adhering the foregoing drug-coated sheet to the inner bottom wall of the container.

Staphylococcus aureua ATCC 25923 was used as a bacterium to be tested, the bacterial cells cultivated overnight on an agar medium were suspended in a sterilized physiological saline at a density of about $10^8$ CFU/ml, followed by diluting it 1000 times (about $10^5$ CFU/ml) with Muller-Hinton broth (composition: meat extract 300 g; casamino acid 17.5 g; starch 1.5 g; purified water 1000 ml), and pouring, at a time, the resulting 20 ml of the broth inoculated with the bacterial cells to be tested into the container. The container was once filled with the broth, but gradually absorbed by the liquid-absorbent body. Ultimately, a desired amount of the broth was retained only on the circular pattern coated with the drug and the excess broth was completely removed after about 30 seconds.

A polyethylene terephthalate sheet having a thickness of 100 μm was adhered to the top of the container for preventing any evaporation and the cultivation was carried out at 35° C. for 16 to 18 hours. After completion of the cultivation, there was determined the drug concentration in the sample-holding portion wherein any growth of the bacteria was not recognized with the naked eyes, which was defined to be MIC value.

The MIC values evaluated in this Example are summarized in the following Table 1.

TABLE 1

| Name of Drug | MIC Value (μg/ml) |
|---|---|
| Piperacillin (PIPC) | 0.5 |
| Oxacillin (MPIPC) | 0.25 |
| Cefazolin (CEZ) | 0.5 |
| Cefmetazole (CMZ) | 1.0 |
| Minocycline (MINO) | 0.25 |
| Ofloxacin (OFLX) | 0.5 |

EXAMPLE 2

Test Instrument According to 1st Embodiment of the Present Invention

A water-absorbing gel layer was formed on an acryl sheet having a length of 8 cm, a width of 12 cm and a thickness of 0.1 cm, in the same manner used in Example 1. Moreover, the same procedures used in Example 1 were repeated to apply a drug onto circular patterns using a dispenser and to form a protective layer thereon.

A liquid-absorbent body having a width of 1 cm and a thickness of 0.8 cm identical to that used in Example 1 was adhered to the peripheral edge of the portions on the base coated with the drug and further a liquid-absorbent body-covering member 4 was formed from the same acryl sheet used above so that the outer side and top face of the liquid-absorbent body were covered.

The test instrument of the present invention thus produced was subjected to the same test for sensitivity to antibacterial agents carried out in Example 1 and the results thus obtained were similar to those observed in Example 1.

EXAMPLE 3

Test Instrument According to 1st Embodiment of the Present Invention

A polystyrene container which comprised a base 1 having a length of 8 cm, a width of 12 cm and a thickness of 0.1 mm and a liquid-absorbent body-covering portion having a width (from the outer edge of the base) of 1 cm was produced by integral injection-molding.

A water-absorbing gel layer was formed on the inner bottom surface of the container in the same manner used in Example 1. Moreover, the same procedures used in Example 1 were repeated to apply a drug onto circular patterns using a dispenser and to form a protective layer thereon.

The space formed between the base and the liquid-absorbent body-covering portion of the container was filled with a liquid-absorbent body identical to that used in Example 1.

The test instrument of the present invention thus produced was subjected to the same test for sensitivity to antibacterial agents carried out in Example 1 and it was confirmed that the results obtained were similar to those observed in Example 1.

EXAMPLE 4

Test Instrument According to 2nd Embodiment of the Present Invention

A test instrument as shown in FIGS. 8 to 10 according to the present invention was produced by the method detailed below.

A polystyrene container was produced by the injection-molding, which was composed of a base portion having a length of 8 cm, a width of 12 cm and a thickness of 5 mm provided with concave portions as sample-holding portions [6(lengthwise)×10(widthwise); 60 portions in all], each having a diameter of 5 mm and a depth of 2.5 mm, and a liquid-absorbent body-covering portion having a height of 1 cm, a width of 1 cm and a thickness of 0.1 mm which was positioned at the peripheral edge of the base, the base and the covering portion being united together.

A drug was applied onto the concave portions of the sample-holding portions using a dispenser by the same method used in Example 1.

The space formed between the base and the liquid-absorbent body-covering portion of the container was filled with a liquid-absorbent body identical to that used in Example 1.

The test instrument of the present invention thus produced was subjected to the same test for sensitivity to antibacterial agents carried out in Example 1 and it was found that the results obtained were similar to those observed in Example 1.

EXAMPLE 5

Test Instrument According to 3rd Embodiment of the Present Invention

A test instrument as shown in FIGS. 11 to 14 according to the present invention was produced by the method detailed below.

A polystyrene sample container having a structure as shown in FIGS. 11 to 14 was produced by the injection-molding. The container had a length of 8 cm, a width of 12 cm and a thickness of 1 cm, was provided with concave portions, on the bottom, as sample-holding portions [6(lengthwise)×12(widthwise); 72 portions in all], each having a diameter of 5 mm and a depth of 2.5 mm, and the level of the bottom face other than the sample-holding portions was lower than that of the peripheral edge of the sample-holding portions.

The peripheral edge of the sample-holding portion is about 5 mm lower than the top of the peripheral wall of the container, the lowest portions each surrounded by 4 sample-holding portions or 2 sample-holding portions at the outer periphery are further 1.5 mm lower than the peripheral edge of the sample-holding portions and openings having a diameter of 1 mm were formed through the lowest positions (91 openings in all).

A drug was applied onto the concave portions of the sample-holding portions using a dispenser by the same method used in Example 1.

A liquid-absorbent body having a length of 6 cm, a width of 10 cm and a thickness of 1 mm (Dripsheet available from Dai Nippon Printing Co., Ltd.) was arranged below the bottom face of the foregoing container so that all of the openings were closed by the body and a polystyrene bottom member produced by injection-molding was fitted to the lower portion of the container.

The test instrument of the present invention thus produced was subjected to the same test for sensitivity to antibacterial agents carried out in Example 1 and it was found that the results obtained were similar to those observed in Example 1.

EXAMPLE 6

Test Instrument According to 4th Embodiment of the Present Invention

A test instrument as shown in FIGS. 20 and 21 according to the present invention was produced by the method detailed below.

There were produced by injection-molding of polystyrene a container having a length of 8 cm, a width of 12 cm and a height of 1 cm provided with concave portions, on the bottom thereof, as sample-holding portions [6(lengthwise)× 10(widthwise); 60 portions in all], each having a diameter of 5 mm and a depth of 2.5 mm, and a cap body which could highly tightly be fitted to the container.

A drug was applied onto the concave portions of the sample-holding portions of the foregoing container using a dispenser by the same method used in Example 1.

To the foregoing cap body, there was adhered grid-like liquid-absorbent body formed from filter paper which had a shape as shown in FIG. 19 and which was present immediately above the portions of the container other than those on which the sample-holding portions were present. When the cap body is fitted to the container, the bottom face of the liquid-absorbent body is almost brought into contact with the inner bottom face of the sample container other than the sample-holding portions.

A broth (80 ml) inoculated with the bacterial cells to be examined identical to that used in Example 1 was poured into the container provided with concave portions at a time to thus fill the container with the broth, then the foregoing cap body was fitted to the container, the broth began to be absorbed by the liquid-absorbent body and after 30 seconds, the excess of the broth other than that to be retained in the concave portions on the sample-holding portions was completely absorbed by the liquid-absorbent body.

Thereafter, the cap body was removed, then the growth of the bacterial cells was observed by the same method used in Example 1 to thus determine the sensitivity of the bacterial cells to the antibacterial agent. The same results observed in Example 1 were obtained.

What is claimed is:

1. An instrument for chemical or microbiological tests comprising;

a sample container for temporarily storing a liquid sample;

a plurality of sample-holding portions formed on the bottom face of the sample container in the form of hydrophilic portions said sample-holding portions being positioned at a level higher than that of the portion on the bottom face of the container other than the sample-holding portion; and a liquid-absorbent body capable of coming in contact with the liquid sample so that the body can absorb the excess sample, when the liquid sample is introduced into the container, while retaining the sample to be held on the sample-holding portions, said liquid-absorbent body being provided such that it constitutes the lowest portion of the bottom face of the container except for the sample-holding portion.

2. The instrument as set forth in claim 1 wherein the sample-holding portions are provided as concave portions on the bottom face of the container.

3. The instrument as set forth in claim 1 wherein the liquid-absorbent body is provided so as to constitute a part or the whole of the bottom face, partly or wholly surrounding the sample-holding portions, of the sample container for accommodating a liquid sample.

4. The instrument as set forth in claim 1 wherein the sample-holding portions contain an agent for a chemical or microbiological test.

5. An instrument for chemical or microbiological tests comprising a sample container for at least temporarily storing a liquid sample; a plurality of sample-holding portions which are arranged on a hydrophobic bottom face of the sample container and spaced apart from one another; a liquid-absorbent body which is provided so as to absorb the liquid sample present at the periphery of the sample-holding portions when the liquid sample is introduced into the container; and a bottom member arranged behind the sample container and capable of supporting the liquid-absorbent body, the bottom member forming a region for accommodating the liquid-absorbent body in cooperation with the sample container, the sample container being provided with a peripheral portion positioned below the sample-holding portion and a through-hole formed on the peripheral portion, and the through-hole permitting the fluid communication with the liquid-absorbent body-accommodating region arranged between the sample container and the bottom member.

6. The instrument of claim 5 wherein the outer peripheral edge of the sample-holding portion is positioned at a level higher than that of the peripheral portion thereof and the peripheral portion is formed from a funnel-like wall body which downward extends from the outer edge towards the hole.

7. The instrument of claim 6 wherein the bottom member is provided with a plurality of upward extending cylindrical standing-up walls and the top face of the standing-up wall has a shape substantially complementary to the lower face of the sample-holding portion.

8. An instrument for chemical or microbiological tests comprising a sample container for at least temporarily storing a liquid sample; a plurality of sample-holding portions which are arranged on a hydrophobic bottom face of the sample container and spaced apart from one another; a liquid-absorbent body which is provided so as to absorb the liquid sample present at the periphery of the sample-holding portions when the liquid sample is introduced into the container; and a bottom member formed in the form of a container whose top is opened, a plurality of cylindrical standing-up walls which upward extend, each having a top face, are formed on the bottom wall of the bottom member, the top face of the standing-up wall constitutes the sample-holding portion; a plurality of through-holes, through which the standing-up wall passes, are formed on the liquid-absorbent body and a plurality of openings capable of being fitted to the top portions of the standing-up walls are formed, on the bottom face of the container.

9. The instrument of claim 8 wherein the standing-up wall is formed in the form of a cylinder and a stepped portion is formed on the outer periphery of the standing-up wall, which is fitted with the inner peripheral edge of the opening on the bottom face to thus position the top edge of the standing-up wall and the bottom face on a substantially the same plane.

10. An instrument for chemical or microbiological tests comprising a sample container for at least temporarily storing a liquid sample; a plurality of sample-holding portions which are arranged on a hydrophobic bottom face of the sample container and spaced apart from one another; a liquid-absorbent body which is provided so as to absorb the liquid sample present at the periphery of the sample-holding portions when the liquid sample is introduced into the container; and a bottom member arranged behind the sample container and capable of supporting the liquid-absorbent body, the bottom member forming a region for accommodating the liquid-absorbent body in cooperation with the sample container, the sample container being provided with a peripheral portion positioned below the sample-holding portion and a through-hole formed on the peripheral portion, and the through-hole permitting the fluid communication with the liquid-absorbent body-accommodating region arranged between the sample container and the bottom member; said bottom member having a bottom wall, wherein upper projections which support the liquid-absorbent body are arranged on the bottom wall of the bottom member and the projections are positioned below the through-holes.

* * * * *

UNITED STATES PATENT AND TRADEMARK OFFICE
CERTIFICATE OF CORRECTION

PATENT NO.   : 5,955,352
DATED        : September 21, 1999
INVENTOR(S)  : Yoshiharu Inoue, et al.

It is certified that error appears in the above-identified patent and that said Letters Patent is hereby corrected as shown below:

Column 2,
Line 54, replace "AA'" with -- 3 --.

Column 3,
Line 7, replace "BB'" with -- 10 --
Line 14, replace "CC'" with --13--
Line 16, replace "DD'" with -- 14 --
Line 19, replace "CC'" wit -- 13 --
Line 41, replace "EE'" with -- 21 --

Column 5,
Line 35, replace "AA'" with -- 3 --

Column 12,
Line 67, replace "BB'" with -- 10 --.

Column 13,
Line 37, replace "CC'" with -- 13 --
Line 39, replace "DD'" with -- 14 --

UNITED STATES PATENT AND TRADEMARK OFFICE
CERTIFICATE OF CORRECTION

PATENT NO. : 5,955,352
DATED : September 21, 1999
INVENTOR(S) : Yoshiharu Inoue, et al.

It is certified that error appears in the above-identified patent and that said Letters Patent is hereby corrected as shown below:

Column 14,
Line 42, replace "CC;" with -- 13 --

Column 17,
Line 18, replace "EE'" with -- 21 --.

Signed and Sealed this

Fourteenth Day of August, 2001

Attest:

NICHOLAS P. GODICI
Attesting Officer     Acting Director of the United States Patent and Trademark Office